(12) United States Patent
Sexton et al.

(10) Patent No.: US 12,055,521 B2
(45) Date of Patent: *Aug. 6, 2024

(54) DETECTION OF BLOCKAGE IN A POROUS MEMBER

(71) Applicant: MSA Technology, LLC, Cranberry Township, PA (US)

(72) Inventors: Robert Kevin Sexton, Butler, PA (US); Nicholas Emidio Ciccone, Allison Park, PA (US); Jerin Miller, Sewickley, PA (US)

(73) Assignee: MSA Technology, LLC, Cranberry Township, PA (US)

( * ) Notice: Subject to any disclaimer, the term of this patent is extended or adjusted under 35 U.S.C. 154(b) by 203 days.

This patent is subject to a terminal disclaimer.

(21) Appl. No.: 17/861,560

(22) Filed: Jul. 11, 2022

(65) Prior Publication Data

US 2022/0349862 A1 Nov. 3, 2022

Related U.S. Application Data

(63) Continuation of application No. 16/874,018, filed on May 14, 2020, now Pat. No. 11,415,562.

(Continued)

(51) Int. Cl.
| | |
|---|---|
| *G01N 29/46* | (2006.01) |
| *G01N 29/04* | (2006.01) |
| *G01N 29/48* | (2006.01) |

(52) U.S. Cl.
CPC ............ *G01N 29/46* (2013.01); *G01N 29/04* (2013.01); *G01N 29/48* (2013.01); *G01N 2291/012* (2013.01)

(58) Field of Classification Search
CPC ... G01N 29/46; G01N 29/48; G01N 2291/012
See application file for complete search history.

(56) References Cited

U.S. PATENT DOCUMENTS 5,576,480 A * 11/1996 Hopkins ............ G01N 15/0826
73/587
5,753,797 A 5/1998 Forster
(Continued)

FOREIGN PATENT DOCUMENTS

| EP | 2104078 | 9/2009 |
|---|---|---|
| EP | 2189956 A2 | 5/2010 |

(Continued)

OTHER PUBLICATIONS

Machine Translation for WO 2019/009379 (Year: 2019).*

*Primary Examiner* — Nathaniel J Kolb
(74) *Attorney, Agent, or Firm* — BARTONY & ASSOCIATES LLC

(57) ABSTRACT

A method of detecting at least a blockage status in a porous member separating a measurement chamber of a device including a gas sensor positioned within the measurement chamber which is responsive to an analyte in an ambient environment to be sampled, includes emitting pressure waves from a pressure wave source which travel within the measurement chamber, measuring a first response via a first sensor responsive to pressure waves positioned at a first position within the measurement chamber, measuring a second response via a second sensor at a second position, different from the first position, and in fluid connection with the pressure wave source, determining the blockage status of the porous member based upon a functional relation of the first response and the second response.

28 Claims, 7 Drawing Sheets

Related U.S. Application Data

(60) Provisional application No. 62/847,705, filed on May 14, 2019.

(56) References Cited

U.S. PATENT DOCUMENTS

| | | | |
|---|---|---|---|
| 5,944,969 | A | 8/1999 | Scheffler |
| 7,034,943 | B1 * | 4/2006 | Moeckli ............... C07K 14/705 |
| | | | 356/423 |
| 7,242,479 | B2 | 7/2007 | Moeckli |
| 7,318,335 | B2 | 1/2008 | Olesen |
| 7,413,645 | B2 | 8/2008 | Scheffler |
| 7,791,475 | B2 | 9/2010 | Clow |
| 7,886,576 | B2 | 2/2011 | Uber |
| 7,959,777 | B2 | 6/2011 | Scheffler |
| 9,528,957 | B2 | 12/2016 | Scheffler |
| 9,784,755 | B2 | 10/2017 | Scheffler |
| 10,788,457 | B2 * | 9/2020 | Miller ................. G01N 33/007 |
| 10,788,458 | B2 * | 9/2020 | Miller .................... G01N 29/11 |
| 10,983,103 | B2 * | 4/2021 | Stokoe ............... G01N 33/0006 |
| 2006/0100796 | A1 * | 5/2006 | Fraden .................... A47L 9/19 |
| | | | 702/50 |
| 2006/0157408 | A1 | 7/2006 | Kuroda |
| 2007/0251221 | A1 * | 11/2007 | Lueschow ............ G01N 29/223 |
| | | | 60/297 |
| 2008/0252891 | A1 | 10/2008 | Uber |
| 2009/0267755 | A1 | 10/2009 | Ropke |
| 2013/0047703 | A1 | 2/2013 | Stengel |
| 2013/0186776 | A1 | 7/2013 | Scheffler |
| 2013/0186777 | A1 | 7/2013 | Scheffler |
| 2013/0192332 | A1 | 8/2013 | Scheffler |
| 2013/0193004 | A1 | 8/2013 | Scheffler |
| 2014/0273263 | A1 | 9/2014 | Zanella, Sr. |
| 2016/0320361 | A1 | 11/2016 | Johansen |
| 2017/0219515 | A1 | 8/2017 | Davis |
| 2017/0227498 | A1 * | 8/2017 | Miller .................. G01N 29/075 |
| 2017/0227499 | A1 * | 8/2017 | Miller .................... G01N 29/11 |
| 2020/0166495 | A1 * | 5/2020 | Stokoe ................. G01N 29/222 |
| 2021/0199635 | A1 * | 7/2021 | Stokoe ................. G01N 29/222 |

FOREIGN PATENT DOCUMENTS

| | | | |
|---|---|---|---|
| JP | 02128298 | 5/1990 | |
| WO | WO2017136559 | 8/2017 | |
| WO | WO-2019009379 A1 * | 1/2019 | ........... B01D 46/442 |
| WO | WO2019009379 A1 | 1/2019 | |
| WO | WO2020106491 | 5/2020 | |
| WO | WO2020232244 | 11/2020 | |

* cited by examiner

DETECTION OF BLOCKAGE IN A POROUS MEMBER

CROSS-REFERENCE TO RELATED APPLICATIONS

This application is a continuation application of U.S. patent application Ser. No. 16/874,018, filed May 14, 2020, which claims benefit of U.S. Provisional Patent Application Ser. No. 62/847,705, filed May 14, 2019, the disclosures of which are incorporated herein by reference.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Many gas sensors include gas porous members/barriers or diffusion barriers that separate or partition the analytical components of the sensor from the environment that the sensor is intended to monitor. Such porous members are commonly used to reduce or eliminate ingress of contaminants that may impede the operation of the sensor's analytical components and/or to isolate the analytical components as a source of ignition in the environment to which the sensor is exposed. When such porous members are used, the analyte gas(es) to be detected/monitored by the sensor must pass through the porous member to reach the analytical components of the sensor. The capability and effectiveness of analyte transport through the porous member directly impacts the speed, precision and accuracy with which the sensor can respond to changes in the relative concentration of the analyte in the external, ambient environment being monitored. As a consequence, porous members are designed and/or selected such that the analyte transport through the porous member, in concert with the analytical components of the sensor, enable the sensor to respond to levels and/or changes in the relative levels of the analyte in the monitored environment at the nominal or minimal rate, precision and accuracy defined by the sensing application. Once a sensor is deployed, extraneous contaminants (arising in the normal operating environment or resulting from atypical events or maintenance activities) contacting or penetrating the porous member can either directly, or as a consequence of reaction with the porous member, inhibit analyte transport between the environment and the analytical components of the sensor. Such an inhibition in analyte transport through the porous member, resulting in deviation from the target sensor response rate to the analyte and/or deviation in precision/accuracy in assessment of absolute or relative changes in analyte concentration, is designated by the term "blockage" or "blocking". Additionally, the contaminant or condition causing the blocking is commonly referred to as the "blockage". A common example of blockage occurs in industrial environments where sensor response to the analyte can become partially or completely inhibited by overpainting, water, dirt/mud, insect or animal deposits, or by other extraneous diffusion-impeding substances. Failure to identify impairment of transport through the sensor porous member can result in under-detection or non-detection of analyte concentration levels exceeding safe environmental limits.

In addition to blockage of a diffusion or other sensor porous member, performance of the sensor itself may degrade over time. Prudence thus dictates that gas detection instrumentation be tested regularly for functionality. It is a common practice to, for example, perform a "bump check," or functionality check on portable gas detection instrumentation on a daily basis. The purpose of this test is to ensure the functionality of the entire gas detection system, commonly referred to as an instrument. A periodic bump check or functionality check may also be performed on a permanent gas detection instrument to, for example, extend the period between full calibrations. Gas detection systems include at least one gas sensor, electronic circuitry and a power supply to drive the sensor, interpret its response and display its response to the user. The systems further include a housing to enclose and protect such components. A bump check typically includes: a) applying a gas of interest (usually the target gas or the analyte gas which the instrument is intended to detect); b) collecting and interpreting the sensor response; and c) indicating to the end user the functional state of the system (that is, whether or not the instrument is properly functioning).

As described above, such bump tests are performed regularly and, typically, daily for portable gas detection instruments. Bump checks provide a relatively high degree of assurance to the user that the gas detection device is working properly. The bump check exercises all the necessary functionalities of all parts of the gas detection device in the same manner necessary to detect an alarm level of a hazardous gas. In that regard, the bump check ensures that there is efficient gas delivery from the outside of the instrument, through any transport paths (including, for example, any protection and/or diffusion member or membranes) to contact the active sensor components. The bump check also ensures that the detection aspect of the sensor itself is working properly and that the sensor provides the proper response function or signal. The bump check further ensures that the sensor is properly connected to its associated power supply and electronic circuitry and that the sensor signal is interpreted properly. Moreover, the bump check ensures that the indicator(s) or user interface(s) (for example, a display and/or an annunciation functionality) of the gas detection instrument is/are functioning as intended.

However, a periodic/daily bump check requirement has a number of significant drawbacks. For example, such bump checks are time consuming, especially in facilities that include many gas detection systems or instruments. The bump check also requires the use of expensive and potentially hazardous calibration gases (that is, the analyte gas or a simulant therefor to which the sensor is responsive). Further, the bump check also requires a specialized gas delivery system, usually including a pressurized gas bottle, a pressure reducing regulator, and tubing and adapters to correctly supply the calibration gas to the instrument. The requirement of a specialized gas delivery system often means that the opportunity to bump check a personal gas detection device is limited in place and time by the availability of the gas delivery equipment.

Recently, a number of systems and methods have been proposed to reduce the number of bump tests required. Such systems may, for example, include electronic interrogation of a sensor and/or a test of the transport path to the sensor, including through a diffusion or other barrier (without application of an analyte gas or a simulant therefor). Nonetheless, it remains desirable to develop improved testing systems and methodologies for reducing the number of bump checks required for sensors.

SUMMARY

In one aspect, a method of detecting at least a blockage status in a porous member separating a measurement chamber of a device including a gas sensor positioned within the measurement chamber which is responsive to an analyte in an ambient environment to be sampled, includes emitting pressure waves from a pressure wave source which travel within the measurement chamber, measuring a first response via a first sensor responsive to pressure waves positioned at a first position within the measurement chamber, measuring a second response via a second sensor at a second position, different from the first position, and in fluid connection with the pressure wave source, determining the blockage status of the porous member based upon a functional relation of the first response and the second response. In a number of embodiments, the second sensor is operated as or used as a reference sensor.

The pressure wave source may, for example, include a speaker and emitting pressure waves which travel within the measurement chamber may include activating the speaker to emit sound waves within the measurement chamber. The first sensor may, for example, include a first microphone, and the second sensor may, for example, include a second microphone.

The second position of the second sensor may, for example, be within a reference chamber that is separated from the measurement chamber but in fluid connection with the speaker. In a number of embodiments, the reference chamber is separated from the measurement chamber by the speaker. The second position of the second sensor may alternatively be within the measurement chamber.

In a number of embodiments, the first response and the second response are measured in the time domain over a period of time and the measured time domain responses are transformed into a frequency domain.

At least one of amplitude and phase may, for example, be determined for each of the first sensor and the second sensor at a frequency. The method may further include determining a ratio of the at least one of the amplitudes and the phases measured by the first sensor and the second sensor. In a number of embodiments, the method includes determining a ratio of each of the amplitudes and the phases measured by the first sensor and the second sensor.

In a number of embodiments, the method further includes comparing a two-dimensional map of the determined ratios of the amplitude and the phase to a previously determined reference map to determine the blockage status of the porous member.

In a number of embodiments, determining the blockage status includes at least one of determining a degree of blockage or a type of blockage in the porous member. In a number of embodiments, the method further includes using a feedback signal from the second sensor to drive a pressure level of the source of pressure waves to a determined level in a close-looped, control methodology.

In another aspect, a gas sensor device to detect an analyte gas in an ambient environment includes a housing comprising a measurement chamber and a port, a porous member in operative connection with the port to separate the measurement chamber from the ambient environment, a sensor responsive to the analyte gas positioned within the measurement chamber, a source of pressure waves positioned within the measurement chamber. a first sensor responsive to pressure waves at a first position within the measurement chamber, a second sensor responsive to pressure waves positioned at a second position, different from the first position, and in fluid connection with the source of pressure waves, and circuitry in operative connection with the first sensor and the second sensor to determine a blockage status of the porous member based upon a functional relation of a response of the first sensor and a response of the second sensor. The second sensor may, for example, be operated as or used as a reference sensor.

In a number of embodiments, the source of pressure waves includes a speaker which emits sound waves when activated. In a number of embodiments, the first sensor comprises a first microphone, and the second sensor comprises a second microphone.

In a number of embodiments, the second position of the second sensor is within a reference chamber that is separated from the measurement chamber but in fluid connection with the speaker. The reference chamber may, for example, be separated from the measurement chamber by the speaker. The second position of the second sensor may alternatively be within the measurement chamber.

In a number of embodiments, the first response and the second response are measured in the time domain over a period of time via the circuitry and the measured time domain responses are transformed into a frequency domain.

In a number of embodiments, at least one of amplitude and phase is determined for each of the first sensor and the second sensor at a frequency. A ratio of response of the first sensor and the second sensor may, for example, be determined via the circuitry. In a number of embodiments, the circuitry determines a ratio of the at least one of the measured amplitudes and the measured phases of the first sensor and the second sensor. In a number of embodiments, the circuitry determines a ratio of each of the measured amplitudes and the measured phases of the first sensor and the second sensor.

In a number of embodiments, the circuitry compares the determined ratios of the measured amplitudes and the measured phases to a previously determined reference map to determine the blockage status of the porous member.

In a number of embodiments, determining the blockage status includes at least one of determining a degree of blockage or a type of blockage in the porous member.

The circuitry may, for example, include a processor system in operative connection with a memory system. In a number of embodiments, the circuitry is further configured to use a feedback signal from the second sensor to drive a pressure level of the source of pressure waves to a determined level in a close-looped, control methodology.

In a further aspect, a method of detecting at least a partial blockage in a porous member separating a first volume of a device from another volume includes emitting pressure waves from a pressure wave source which travel within the first volume, measuring a first response via a first sensor responsive to pressure waves positioned at a first position within the first volume, measuring a second response via a second sensor at a second position, different from the first position, and in fluid connection with the pressure wave source, determining an operational status of the porous member based upon a functional relation of the first response and the second response. The second sensor may, for example, be operated as or used as a reference sensor. In a number of embodiments, the pressure wave source includes a speaker and emitting pressure waves which travel within the first volume comprises activating the speaker to emit sound waves within the first volume. In a number of embodiments, the first sensor comprises a first microphone, and the second sensor comprises a second microphone.

In another aspect, a device includes a housing comprising a first volume and a port, a porous member in operative connection with the port to separate the first volume from another volume, a source of pressure waves positioned within the first volume, a first sensor responsive to pressure waves at a first position within the first volume, a second sensor responsive to pressure waves positioned at a second position, different from the first position, and in fluid connection with the source of pressure waves, and circuitry in operative connection with the first sensor and the second sensor to determining an operational status of the porous member based upon a functional relation of a response the first sensor and a response of the second sensor. The second sensor may, for example, be operated as or used as a reference sensor. In a number of embodiments, the source of pressure waves includes a speaker which emits sound waves when activated. In a number of embodiments, the first sensor comprises a first microphone, and the second sensor comprises a second microphone.

A number of embodiments of devices, system and methods hereof thus include a pressure wave source such as a speaker, a first sensor (for example, a first microphone) and a second, reference sensor (for example, a second microphone). An acoustic guide may be divided into two acoustic chambers: a measurement chamber including the first sensor and a reference chamber including the second sensor. Alternatively, the acoustic guide may include only a measurement chamber in which the first sensor and the second, reference sensor are positioned. The pressure wave source/speaker may emit one or more tones/frequencies which are channeled to the first and second sensors.

In a further embodiment, a method of detecting at least a blockage status in a porous member separating a measurement chamber of a device including a gas sensor positioned within the measurement chamber which is responsive to an analyte in an ambient environment to be sampled includes emitting pressure waves from a pressure wave source which travel within the measurement chamber, measuring a first response via a first sensor responsive to pressure waves positioned at a first position within the measurement chamber, measuring at least one reference variable related to a change in output of the pressure wave source arising from a condition other than a control input thereto, and determining the blockage status of the porous member based upon a functional relation of the first response and the at least one reference variable. Input to the pressure wave source may, for example, be monitored and/or a response estimated. In a number of embodiments, the pressure wave source is a speaker and the reference variable is determined via measuring at least one of speaker drive voltage or current directly or is determined in conjunction with a predictive model utilizing predetermined, estimated or measured electrical and mechanical parameters of the speaker. In a number of embodiments, the at least one reference variable is measured via a response of a second sensor responsive to pressure waves positioned at a second position, different from the first position, and in fluid connection with the source of pressure waves.

In still a further aspect, a device includes a housing including a first volume and a port, a porous member in operative connection with the port to separate the first volume from another volume, a source of pressure waves positioned within the first volume, a first sensor responsive to pressure waves at a first position within the first volume, and circuitry in operative connection with the first sensor and with the source of pressure waves. The circuitry is configured to determine at least one reference variable related to a change in output of the pressure wave source arising from a condition other than a control input thereto and to determine an operational status of the porous member based upon a functional relation of a response the first sensor and the at least one reference variable.

The devices, systems and methods hereof do not require precise control over the output level of the speaker and provide for more uniform grouping of responses from unit to unit, thereby making the detection of blockage states or conditions easier while also giving the system improved immunity to false detection. Blockage state or status determination becomes much more reliable when a second, reference sensor (for example, microphone) is used to provide a reference measurement of the pressure wave source's/ speaker's output. Without such a reference measurement, the true or actual output of the pressure wave source/speaker and change in the output thereof arising from conditions such as an environmental shift or material fatigue may potentially be confused with a change caused by a blockage of the porous member. A reference measurement also assists in generating a more uniform response for blockage types from unit to unit.

The present devices, systems, and methods, along with the attributes and attendant advantages thereof, will best be appreciated and understood in view of the following detailed description taken in conjunction with the accompanying drawings.

DETAILED DESCRIPTION

Figure 1A:
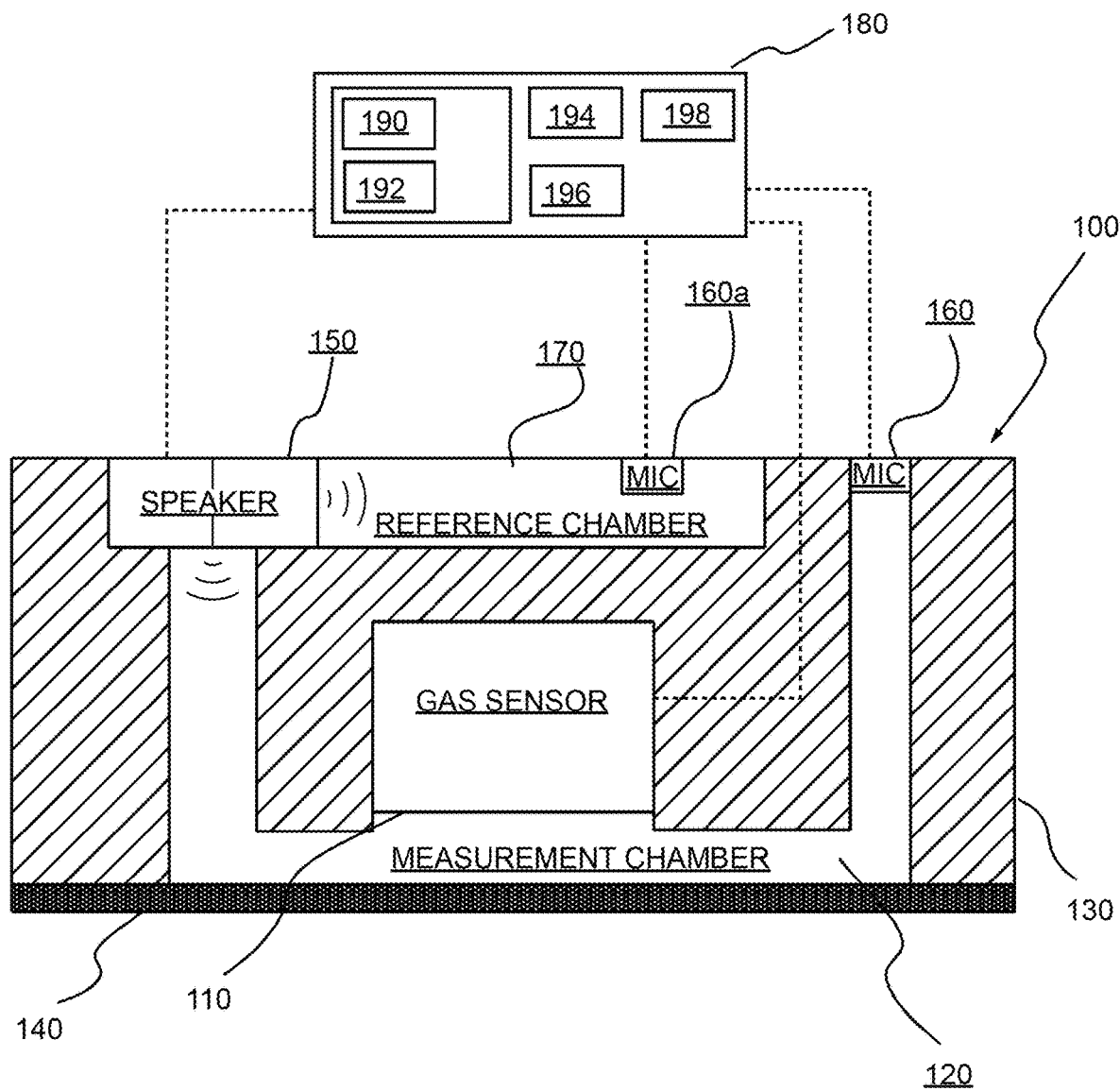
FIG. 1A illustrates an embodiment of a gas sensor device hereof including a first of measurement microphone and a second or reference microphone.

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of various embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a sensor" includes a plurality of such sensors and equivalents thereof known to those skilled in the art, and so forth, and reference to "the sensor" is a reference to one or more such sensors and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

As used herein, the term "circuit" or "circuitry" includes. but is not limited to, hardware, firmware, software or combinations of each to perform a function(s) or an action(s). For example, based on a desired feature or need. a circuit may include a software controlled microprocessor, discrete logic such as an application specific integrated circuit (ASIC), or other programmed logic device. A circuit may also be fully embodied as software.

The term "control system" or "controller," as used herein includes, but is not limited to, any circuit or device that coordinates and controls the operation of one or more input or output devices. For example, a controller can include a device having one or more processors, microprocessors, or central processing units (CPUs) capable of being programmed to perform input or output functions.

The term "processor," as used herein includes, but is not limited to, one or more processor systems or stand-alone processors, such as microprocessors, microcontrollers, central processing units (CPUs), and digital signal processors (DSPs), in any combination. A processor may be associated with various other circuits that support operation of the processor, such as a memory system (for example, random access memory (RAM), read-only memory (ROM), programmable read-only memory (PROM), erasable programmable read only memory (EPROM)), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

As a metric, blockage may directly designate impedance of analyte transport through a porous member and/or designate the consequential changes in sensor performance resulting from this transport impedance. Blockage may, for example, be metered in a continuous measure. For example, blockage may be metered as a percentage, ranging from 0% when analyte transport through the porous member is normal or nominal to 100% marking total inhibition of analyte transport between the sensor analytical components and the monitored environment. Blockage may also be metered as discrete states with designations such as unblocked (indicating typical or normal analyte transport through the porous member) or partial (indicating impedance of analyte transport beyond typical or normal but less than complete transport inhibition) or complete (indicating total inhibition of analyte transport through the porous member). Alternatively, blockage can be ascribed to Boolean states, with an unblocked state indicating inhibition of analyte transport through the porous member falls below a designated acceptable limit, and a blocked state indicating analyte transport inhibition exceeds the designated limit. Adequate measure in detecting and designating blockage (and/or resultant impairment to sensor performance) is important for assurance of sensor function. Failure to identify impairment of transport through the sensor porous member can result in underdetection or non-detection of analyte concentration levels exceeding safe environmental limits.

In a number of embodiments, devices, systems and methods hereof are used to detect flow through a porous member, membrane or barrier (for example, a diffusion barrier) of, for example, a sensor for detecting a target or an analyte gas. Such porous members may, for example, be porous metal frits or porous polymeric membranes in a number of representative embodiments. In a number of embodiments, a source, generator or transmitter of pressure waves or acoustic waves such as a speaker is activated within an inner or measurement volume or chamber behind (that is, on the sensor side and opposite the ambient side) a porous member such as a porous frit or a porous membrane. A response to the generated acoustic/pressure waves (for example, sound) is measured by a first pressure wave sensor, acoustic sensor or receiver such as a microphone and is relatable to gas transport through the membrane. A second pressure wave sensor or receiver such as a microphone is provided at a different position from the first pressure wave sensor or receiver to provide a reference signal. In general, any sensor or receiver that is responsive to pressure changes or waves of pressure propagated in a medium (for example, air) may be used herein. Such sensors or receivers are sometimes referred to herein generally as acoustic sensors or receivers.

In a number of representative embodiments, the present devices, systems and methods may, for example, be used in fixed or portable gas instruments. In the case of a fixed (as opposed to portable) gas instrument, the instrument is calibrated when it is put into service. As described above, after placement in service, it is recommended to frequently "bump test" the instrument to check for gas flow to the sensor and that the sensor responds as expected. As also described above, to bump test an instrument, the user applies a target/analyte gas (or a simulant gas to which the sensor is responsive) of a known concentration to the instrument and checks the instrument for an expected or acceptable response. If the sensor response is acceptable (using, for example, predetermined thresholds), the user can then calibrate the instrument to the known concentration of the target gas.

By using electronic interrogation systems and methods as described, for example, in U.S. Pat. Nos. 7,413,645, 7,959,777 and U.S. Patent Application Publication Nos. 2014/0273263, 2013/0193004, 2013/0192332, 2013/0186776, 2013/0186777, and U.S. patent application Ser. No. 15/012,919, the disclosures of which are incorporated herein by reference, one has the ability to electronically interrogate a sensor, determine changes in sensor performance thereby, and compensate sensor output so that the sensor response is acceptable, thereby extending the period of time between (or eliminating) bump checks. Electronic interrogation of a sensor may, for example, include applying electrical energy to an electrode or sensor element and measuring a response to the application of electrical energy and/or an electrical property of the electrode or sensor element to determine a state of the sensor. Electronically interrogating a sensor, however, cannot account for or detect blockage of the porous member that separates/protects the sensor from the ambient environment or outside world. Combining electronic interrogation of the sensor with systems, devices and methods of detecting blockage of such a porous member, provides the ability to further reduce or eliminate bump testing the instrument.

In a number of representative embodiments hereof, to detect a blockage of a porous member separating a gas sensor from the ambient environment (in which the concentration of the analyte gas is to be determined) an acoustic wave or waves transmitted from a source/speaker interacts with the porous member and with any blockage thereof. Signals are received by the first sensor (pressure wave or acoustic sensor/microphone) which is positioned within a measurement chamber to be excited by both the output of the pressure wave source/speaker and reflectance from the porous member. A second sensor (pressure wave or acoustic sensor/microphone; at a different position than the first sensor) is operated as a reference sensor and may be excited by output from the pressure wave source/speaker only or by both output of the pressure wave source/speaker and reflectance from the porous member. The response of the first sensor and the response of a second, reference sensor are processed and correlated to a loss in flow through the porous member (that is, a blockage state) and/or, in the case of a gas sensor, a loss in gas response of the gas sensor. There are a number of ways to analyze and/or to process the data to determine the presence and/or degree of a blockage. In a number of embodiments, the source/speaker and the first sensor are positioned or located on the same side of the porous member as the gas sensor (that is, within a measurement volume or chamber including the gas sensor, which is in fluid connection with the porous member). In a number of embodiments, the source of pressure waves (for example, a speaker) is positioned within the chamber, spaced from the porous member. In general, substantially all or all pressure waves emitted from the source of pressure waves that are transmitted out of the chamber are transmitted through the porous member in such embodiments. For example, less than 10%, less than 5% or less than 2% of pressure waves emitted from the source of pressure waves may be transmitted out of the chamber other than through the porous member in such embodiments. The second sensor may be positioned in a reference volume or chamber which is isolated from reflectance from the porous member or within the measurement volume of chamber (but at a different position therein from the first sensor).

Figure 1B:
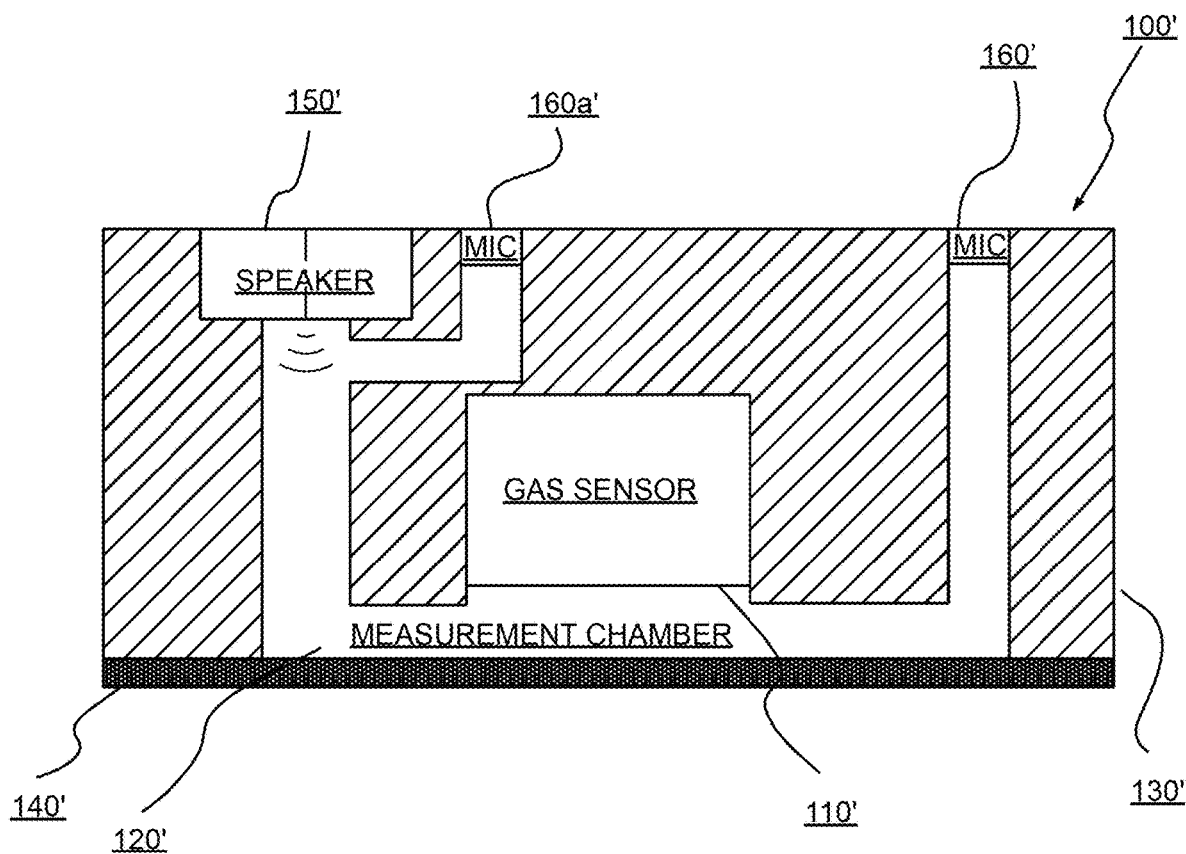
FIG. 1B illustrates another embodiment of a gas sensor device hereof including a first of measurement microphone and a second or reference microphone.
Figure 2:
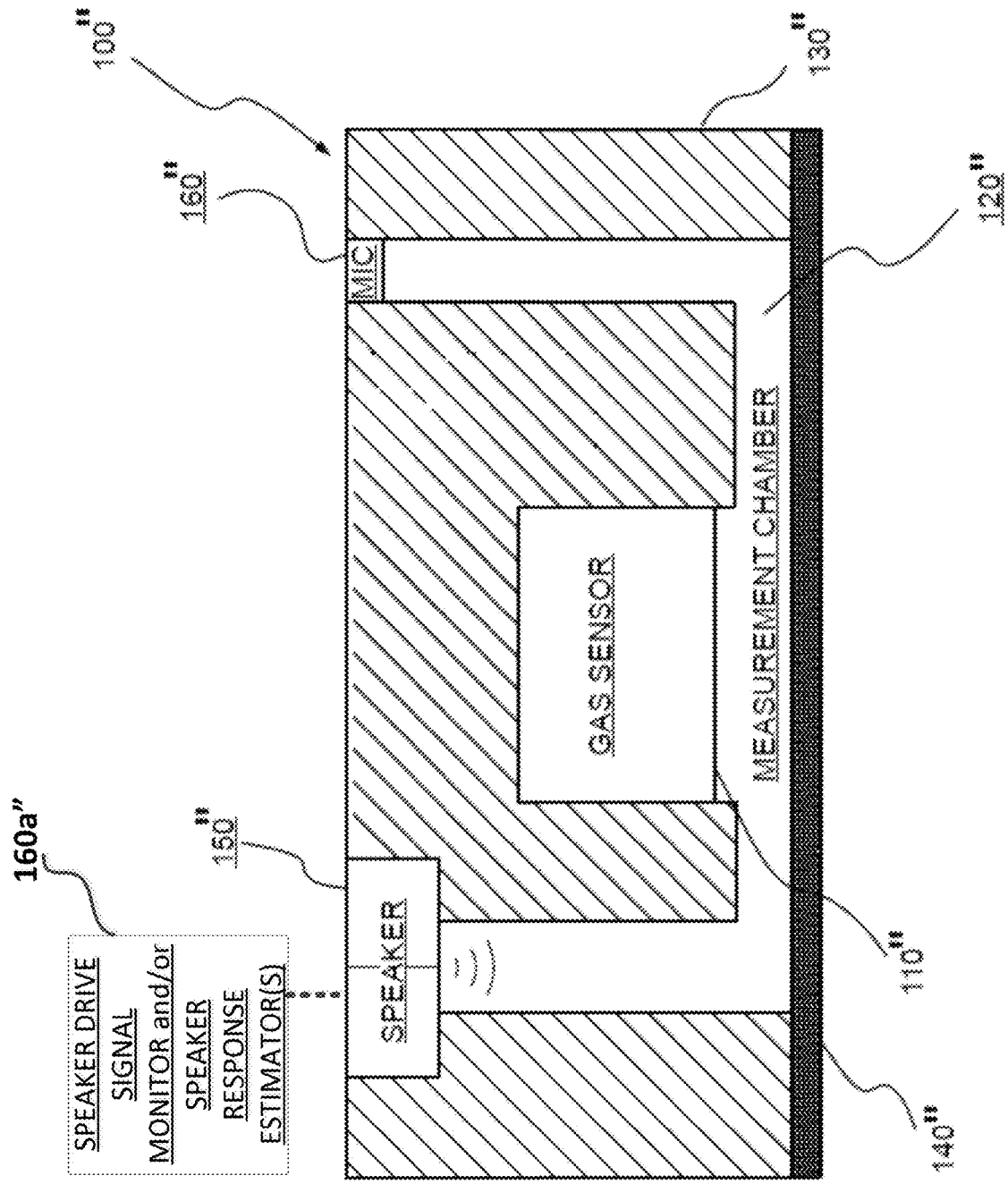
FIG. 2 illustrates another embodiment of a gas sensor device hereof in which a drive signal is monitored or a response estimated for a pressure wave source or speaker.

Several embodiment of devices hereof are illustrated in FIGS. 1A, 1B and 2. In a number of studied embodiments hereof, a device 100 such as a combustible gas sensor device (see FIG. 1A) was tested which included a sensor 110 within an inner or measurement volume or chamber 120 created by an explosion-proof housing 130 and a porous member in the form of a porous frit 140. Catalytic combustible gas sensor devices and electronic interrogation thereof are, for example, described in U.S. Patent Application Publication No. 2014/0273263, the disclosure of which is incorporated herein by reference. Although combustible gas sensors were studied in a number of representative embodiments hereof, the devices, systems and method hereof can be used in connection with any sensor (for example, electrochemical sensors, photoacoustic sensors, etc.) or other device in which a porous member or membrane separates an inner chamber or volume from another volume (for example, an outside environment). In the embodiment of device 100, a pressure wave source (that is, an electromotive transducer to convert electrical energy into pressure waves) in the form of speaker 150 and a first pressure wave sensor (first sensor) in the form of first microphone 160 are also positioned within chamber 120. Although, it is not necessary to acoustically isolate speaker 150 and first microphone 160 from the remainder of chamber 120 and sensor 110 or to narrowly channel the propagation of acoustic/pressure waves therebetween, separation/isolation of microphone 160 from a second (reference) microphone 160a and/or channeling to preferentially couple microphone 160 to a porous member or frit 140 hereof (and/or to preferentially couple second microphone 160a to speaker 150) may, for example, assist in providing discrimination between various blockage states of porous member or frit 140 as discussed further below.

In the illustrated embodiment, sensor 110, speaker 150, first microphone 160 and second (reference) microphone 160a (discussed further below) are in electrical connection with circuitry or electronic circuitry 180 (for example, via a printed circuit board or PCB, not shown) which may include control circuitry including, for example, a processor system 190 (including one or more processors such as microprocessors) and a memory system 192 in operative connection with processor system 190. Memory system 192 may, for example, include one or more algorithms/software stored therein and executable by processor system 190. The user may be provided data/information and/or may input data/information via a user interface system 194 (including, for example, a visual display system, an audio system, and/or a tactile system for providing data/information to a user and one or more data input systems such as a touch screen, a keyboard, a mouse, etc. for input of data/information). A communication system 196 (including for example, a receiver and/or a transmitter) may be provided for communication (for example, data/information communication) between device 100 and a remote device or system. Data communication system 196 may, for example, provide for wired and/or wireless communication. A power system 198, which may include one or more batteries in the case of a portable device or line power in the case of a fixed device, is provided to power circuitry 180.

As described, for example, in U.S. Patent Application Publication No. 2017/0227498 and U.S. Patent Application Publication No. 2017/0227499, the disclosures of which are incorporated herein by reference, acoustic waves propagate within chamber 120 toward frit 140. Without limitation to any mechanism, some of the acoustic waves pass into frit 140, and some of the pressure/sound waves are reflected back into inner chamber 120. In that regard, of the acoustic waves that pass into frit 140, some are absorbed in frit 140, some are reflected back into measurement chamber 120 (from which the acoustic waves emanated), and some pass through frit 140 into the ambient environment outside of explosion proof housing 130. The acoustic waves that are passed through frit 140 and outside of explosion-proof housing 130 are "lost" acoustic waves, which are relevant to the degree of blockage of fit 140. When frit 140 is blocked, less acoustic waves (for example, sound waves) are lost, and more acoustic waves are reflected back into chamber 120. In a number of studies, one or more frequencies may be generated by speaker 150. In a number of studies, sound was emitted from speaker 150 at a single frequency.

Pressure wave sources such as speakers exhibit a significant amount of variability in output signal (for example, magnitude and/or phase) resulting from a given or determined applied input signal/input energy from one speaker to another, even at the time of manufacture. Moreover, output may for a given input signal may change over time as a result of changes in components of the pressure wave source/speaker. One cannot produce an output signal for a given input signal/energy and predict with certainty what the resultant magnitude and phase thereof will be. Further, the speaker output will vary with environmental conditions such as temperature, pressure etc. Still further, variation in the blockage state of porous member or frit 140 will also affect the speaker output for a given applied input signal/energy. In other words, the output from speaker 150 will vary with the variable to be measured (that is, the blockage state frit 140). Thus, applying of the same voltage to speaker 150 over time will result in different output because of conditions.

In a number of embodiments hereof, compensation is made for variation in speaker output arising from changes other than a change in input signal/energy (for example, changes arising from differences in speakers, changes in environmental conditions and/or changes in the blockage state of a porous member such as frit 140. One may, for example, utilize speaker impedance or back emf determined from measurements of speaker drive voltage and/or currents directly or in conjunction with for example, predictive models utilizing predetermined, estimated or measured electrical and mechanical parameters of the speaker, to account for such changes in speaker output. However, accurate or repeatable correlation of speaker output to monitored speaker drive voltage and/or currents or predictive models using these monitored signals is difficult. Though difficult, a functional relationship between the measured back emf or speaker input impedance or direct measure of input voltage and/or current and the output of measurement speaker such as speaker 150 may be used to compensate for the changes in speaker output described above. As described further below, in some instances, it may be possible to substitute the magnitude and/or phase determined from measured speaker drive current or voltage or estimated back emf or speaker impedance in place of, for instance, the magnitude and phase of a second reference microphone in a frequency response function (FRF) relation described herein. However, providing a second, reference microphone provides a significantly improved measurement to achieve the discrimination desirable in the devices, systems and methods hereof.

In that regard, to account for variations in output for a given energy input between different speakers and with variation in conditions in a number of embodiments hereof, a second, reference sensor, in the form of reference microphone 160a is provided at a position different from the position of first microphone 160 in device 100. The blockage status of a porous member is determined through a functional relation of a response of microphone 160 and a response of reference microphone 160a.

In the embodiment of device 100, second microphone 160a is positioned within a reference volume or chamber 170. Reference chamber 170 is in fluid connection or acoustic connection (via the air or other gas therein) with speaker 150. In that regard, pressure waves or sound output from speaker 150 reaches second microphone 160a. However, reference chamber 170 and second microphone 160a therein are isolated from measurement chamber 120 and porous frit or member 140. Although the blockage state of porous member 140 still affects the output of speaker 150 as measured by second microphone 160a, second microphone 160a monitors only the speaker output. Second microphone 160a is not excited by the reflectance from porous fit or member 140. In the embodiment of FIG. 1A, reference volume or chamber 170 is isolated from measurement volume or chamber 120 and from porous frit 140 by speaker 150. Measurement chamber 120 may, for example, be sealed to and in fluid or acoustic connection with a first output of front of speaker 150, while reference chamber 170 may be in fluid or acoustic connection with a second output or back of speaker 150. Reference chamber 170 may, for example, be connected to and sealed with a back side of speaker 150.

Analysis of response of the first sensor and second, reference sensor hereof may, for example, be made in the time domain or in the frequency domain. In the frequency domain, one may, for example, analyze magnitude and/or phase of response. In the time domain, one may, for example, analyze magnitude and/or time delay of a response. Various analytic techniques as discussed in U.S. Patent Application Publication No. 2017/0227498 and U.S. Patent Application Publication No. 2017/0227499 may, for example, be modified for use in connection with the output/response from a second, reference sensor hereof.

Figure 3:
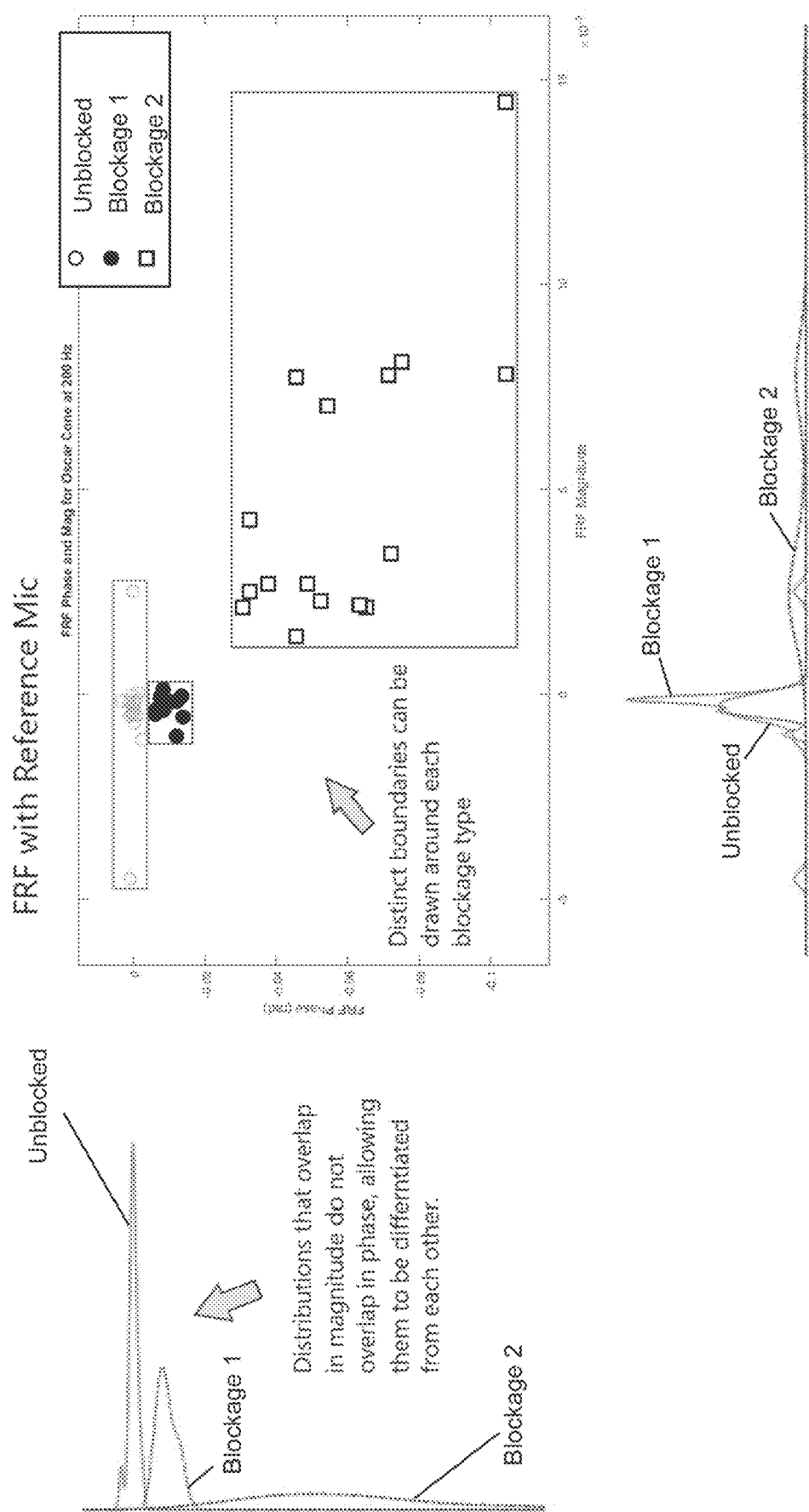
FIG. 3 illustrates a two-dimensional graph or map of a frequency response function (FRF) determined from Fourier transforms of time domain responses for a first microphone and a second (reference) microphone, illustrating regions associated with blockage states of the porous member.

In a number of embodiments, a Fourier transform (for example, a fast Fourier Transform or FFT) was used to convert response data from the time domain to the frequency domain. Other transforms may be used. In a number of embodiments, the data from first microphone 160 and second microphone 160a were co-sampled over a predetermined length of sample. Co-sampling is a method of analysis using phase from a Fourier transform. By co-sampling it is meant that the samples are taken at the same rate and a fixed interval of time between the two sensors. A Fourier transform was performed on the data at a frequency of interest. A frequency response function (FRF) was determined using a functional relationship (for example, a ratio) of two Fourier terms. A ratio of measured magnitude from first microphone 160 and second microphone 160a was determined in a number of embodiments. In the illustrated embodiment of FIG. 3, magnitude from first microphone 160 was in the numerator and magnitude from second, reference microphone 160a was in the denominator). In other embodiments, the numerator and denominator may be reversed to determine an inverse FRF. Likewise, an offset of measured phase of the first microphone 160 relative to the second microphone 160a was determined. In the illustrated embodiment of FIG. 3, the complex phase from first microphone 160 was in the numerator and the complex phase from second, reference microphone 160a was in the denominator. The phase ratio is equivalent to the difference of phase in the numerator minus phase in the denominator. In FIG. 3, the magnitude ratio and phase offset/difference are plotted on a two-dimensional map. The locus or region of points (phase ratio/difference, magnitude ratio pairs) on the map of FIG. 3 provides information regarding a blockage state. In the data of FIG. 3, three different blockage states were studied. As illustrated in FIG. 3, distributions that may overlap in magnitude, did not overlap in phase, allowing differentiation in the two-dimensional map. Thus, determined ranges of values of data pairs of phase ratio/difference and magnitude ratio may be associated with various blockage states. As a representative example, the methods and calculations employed to generate each of the FRF points mapped in FIG. 3 are discussed below.

In a number of embodiments, a sine wave Sig_spkr is generated to drive the speaker using a digital-to-analog converter or DAC with sample frequency Fs of 8 kSamp/sec to create a tone at ftone=200 Hz as mic1 (measurement microphone) and mic2 (reference microphone) are simultaneously sampled at 8 kSamp/sec. In a number of embodiments, the frequency ftone is selected based primarily on sensitivity of acoustic response to blockage conditions and so that an integer number of $2*\pi$ cycles of ftone sampled at Fs at the microphones will fit in a discrete buffer of length N related to discreate Fourier transform or DFT calculations for the microphone signals. Sig_spkr[nspk]=A*sin($2*\pi$*ftone/Fs*nspk) which creates a cycle each time the integer sample index nspk reaches increments of Fs/ftone samples. The amplitude A may be chosen to provide adequate margin to background noise while not saturating the speaker or microphones.

In a number of embodiments, at nspk=1780, recording of the samples from mic1 and mic2 is initiated into respective 8 k sample buffers, that is the n=1 sample captured and recorded for the microphones is coincident with the playing of the nspk=1780 speaker sample. Recording and speaker drive signal generation stop after the respective microphone data buffers are filled at 8000 samples (nspkr=9780 and n=8000). This results in 40 complete cycles of 200 Hz sine wave data recorded in the respective microphone buffers. The buffer size of 8000 samples is chosen to achieve a resolution bandwidth=Fs/N of 1 Hz for the discrete Fourier transform (DFT) and so that ftone resides in the center of the DFT transform bin. Additionally, the buffer size N is chosen to capture an integer number of $2*\pi$ cycles of ftone at sample rate Fs to simplify and reduce the computation of the DFT by eliminating the need to include a windowing function (for example Hamming or Hanning windows) that multiplies with every sample in the buffer applied to the DFT to reduce or eliminate spectral bleeding of information at ftone into other DFT bins and to the ftone bin from other frequencies.

Figure 4:
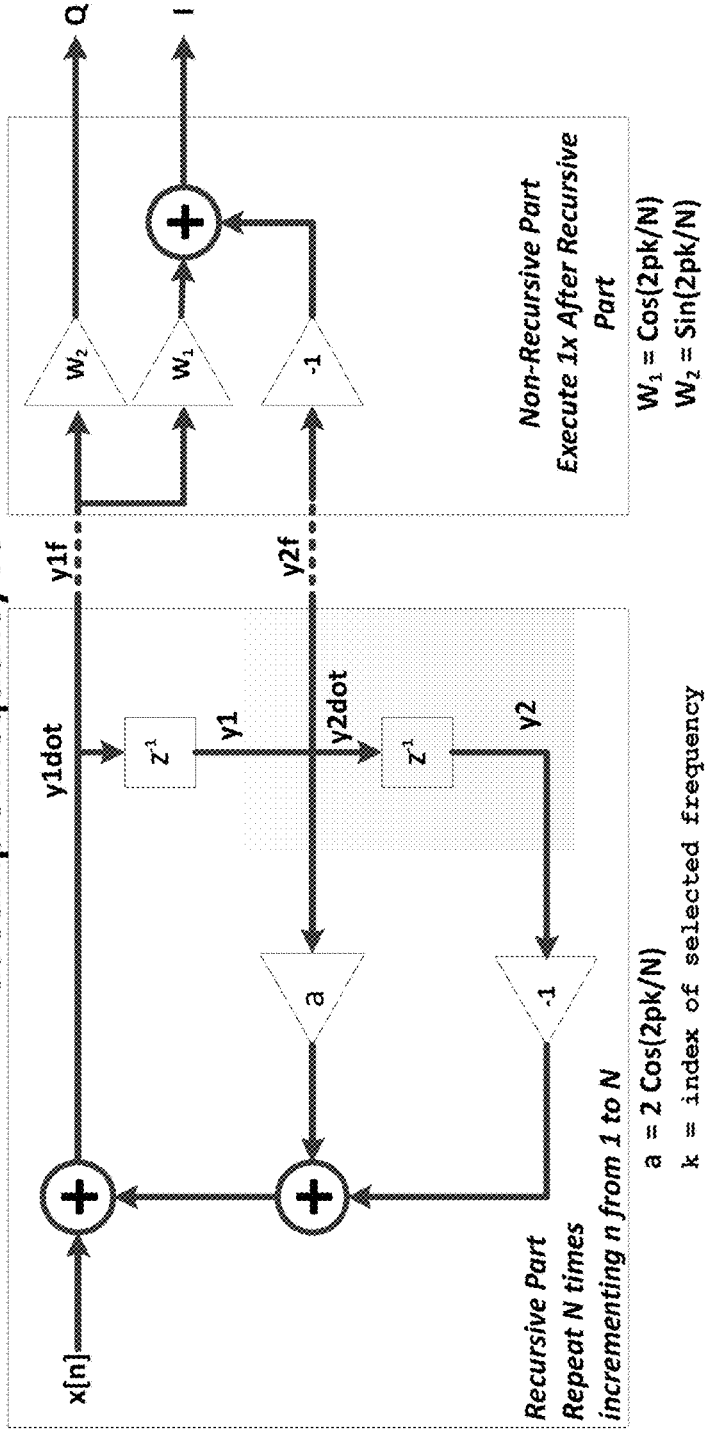
FIG. 4 illustrates an embodiment of the Goertzel discrete Fourier transform (DFT) algorithm used in a number of embodiments hereof.

The sampled data from each microphone buffer is transformed into a single frequency discrete Fourier transform using a computationally efficient Goertzel algorithm as illustrated in FIG. 4 and described below. While any computational form of the DFT may be utilized to calculate the frequency transforms of the microphone signals, the Goertzel implementation of the DFT is appropriate for this application as the microphone signals x[n] are real-valued. Unlike direct DFT which utilizes complex-valued coefficients and calculations, the Goertzel algorithm is more efficient and applies a single real-valued coefficient at each iteration, using real-valued arithmetic for the real-valued input sequences.

The Goertzel algorithm utilizes three constants precalculated and stored in memory. All three of these constant terms are derived from a common phase term $2\pi k/N$ that is unique to the single frequency ftone at which the DFT is calculated. Here N is the number of samples applied to the DFT and k is an integer k=(ftone/Fs)*N where Fs is the sampling frequency at which the microphone samples x[n] are acquired. A real-valued filter coefficient term $\alpha=2\,Cos(2\pi k/N)$. Two basis function terms (twiddle factor terms) utilized in the final non-recursive stage to separate the real and imaginary output terms of the DFT are set forth below:

$W1=Cos(2\pi k/N)$(coefficient for real part of DFT(*I*))

$W_2=Sin(2\pi k/N)$(coefficient for imaginary part of DFT(*Q*))

The DFT's for mic1 (measurement microphone) and mic2 (reference microphone) are calculated separately using the Goertzel algorithm identified in FIG. 4. The calculation begins by processing all N samples of the buffer using the recursive partition of the algorithm depicted in left rectangular region of FIG. 4 with the following recursive state-space computations:

$$\begin{bmatrix} y1dot \\ y2dot \end{bmatrix} = \begin{bmatrix} \alpha & -1 \\ 1 & 0 \end{bmatrix} * \begin{bmatrix} y1 \\ y2 \end{bmatrix} + \begin{bmatrix} 1 \\ 0 \end{bmatrix} * x[n]$$

At each sample n in the respective microphone signal x[n], the values of the state variables y1dot, y2dot, y1 and y2 depicted in FIG. 4 are recursively updated N times as follows as n is incremented from 1 to N as follows:
For n=1 to N $y1dot=y1*\alpha-y2+x[n]$;

$y2dot=y1$;

$y1=y1dot$;

$y2=y2dot$;

It is not necessary that the N samples for each microphone signal x[n] be recorded into a buffer as the calculations described above may be performed as each sample x[n] is acquired. Utilization of a buffer simply allows the sampling and computations to be carried out at a time different times. Following the Nth iteration, the values of y1dot and y2dot are passed to the non-recursive part of the computation to calculate the real (I) and imaginary (Q) parts of the DFT (as set forth below). In FIG. 4, y1f=y1dot and y2f=y2dot come from the Nth iteration of the recursive calculations.

$I=W1*y1f-y2f=Cos(2\pi k/N)*y1f-y2f$;

$Q=W2*y2f=Sin(2\pi k/N)*y2f$.

The calculations described above are carried out separately for the data sampled simultaneously for mic 1 ($x_{mic1}$[n]) and mic 2 ($x_{mic2}$[n]) to produce the following discrete frequency transforms $X_{mic1}$ and $X_{mic2}$ respectively:

$X_{mic1}=I1+i*Q1$ where $i=sqrt(-1)$ for imaginary part $Q$ $X_{mic2}=I2*i*Q2$

The frequency response functions that are mapped to a classification map such as depicted in FIG. 3 are calculated as a ratio in the DFT from the measurement microphone (mic1) to the reference microphone (mic2)

$FRF=X_{mic1}/X_{mic2}$.

To compute the FRF, it is convenient to convert $X_{mic1}$ and $X_{mic2}$ computed in rectangular form (I+i*Q) to exponential polar form $r*e^{i\theta}$. where $r=sqrt(I^2+Q^2)$ and $\theta=tan^{-1}(Q/I)$ where $tan^{-1}$ in this case represents the four quadrant arctangent atan 2(Q,I) that returns a single value $\theta$ such that $-\pi<\theta\leq\pi$ such that $I=r*Cos(\theta)$ and $Q=r*Sin(\theta)$.

$X_{mic1} = I_{mic1} + i * Q_{mic1} = M * e^{i\theta M}$ $X_{mic2} = I_{mic2} + i * Q_{mic2} = R * e^{i\theta R}$ With this formulation, the magnitude and phase terms of the FRF mapped to the classification map may be calculated as follows:

$$FRF = X_{mic1}/X_{mic2}$$
$$= M * e^{i\theta M}/(R * e^{i\theta R})$$
$$= M/R e^{i(\theta M - \theta R)}$$
$$FRF \text{ Magnitude} = M/R;$$
$$FRF \text{ Phase} = \theta M - \theta R;$$

Thus, the FRF magnitude represents a ratio of the magnitude of signal M from a measurement microphone (mic1) positioned and connected for acoustic coupling with the porous member to the magnitude of a signal R from a reference microphone (mic2) positioned and connected for acoustic coupling and tracking of the sound generated by the speaker. Through this ratio, variances in the signal received at mic 1 due to changes in the speaker acoustic output level metered at mic 2 are effectively cancelled out such that the FRF magnitude allows discrimination of changes in the amplitude of the signal at mic 1 due to changes in the blockage of the porous member from changes due to variance in the speaker output level.

Likewise, the FRF phase represents the difference in the phase θM of the signal from microphone 1 connected to monitor the combined response of the speaker and reflections from the porous member and the phase θR from microphone 2 located and connected to respond to the speaker output. Thus utilization of the FRF phase=θM−θR enables variances in the speaker phase to be separated from changes in phase at mic1 θM caused by changes in acoustic response of the porous member due to blockage.

As a further aspect of identification and/or detection of blockage of the porous member, it is convenient to project the FRF calculated following each acoustic interrogation of the system to a blockage classification map with FRF magnitude mapped as an x-axis coordinate and FRF phase mapped as a y-axis coordinate as illustrated in FIG. 3. With variances in the acoustic output of the speaker effectively tracked and removed by the FRF, the FRF's from different interrogations map to regions on the map that uniquely correlate with blockage conditions of the porous member as identified by the rectangular box regions in FIG. 3. Using a correlation map such as this, it is possible to classify the blockage condition of the porous fit by identifying the region of the map on which the FRF is located. For example, in the correlation map of FIG. 3, FRF's that fall on or within the boundary of the middle rectangular box correlate with blockage type 1 and those in the large rectangle with blockage type 2.

Figure 5:
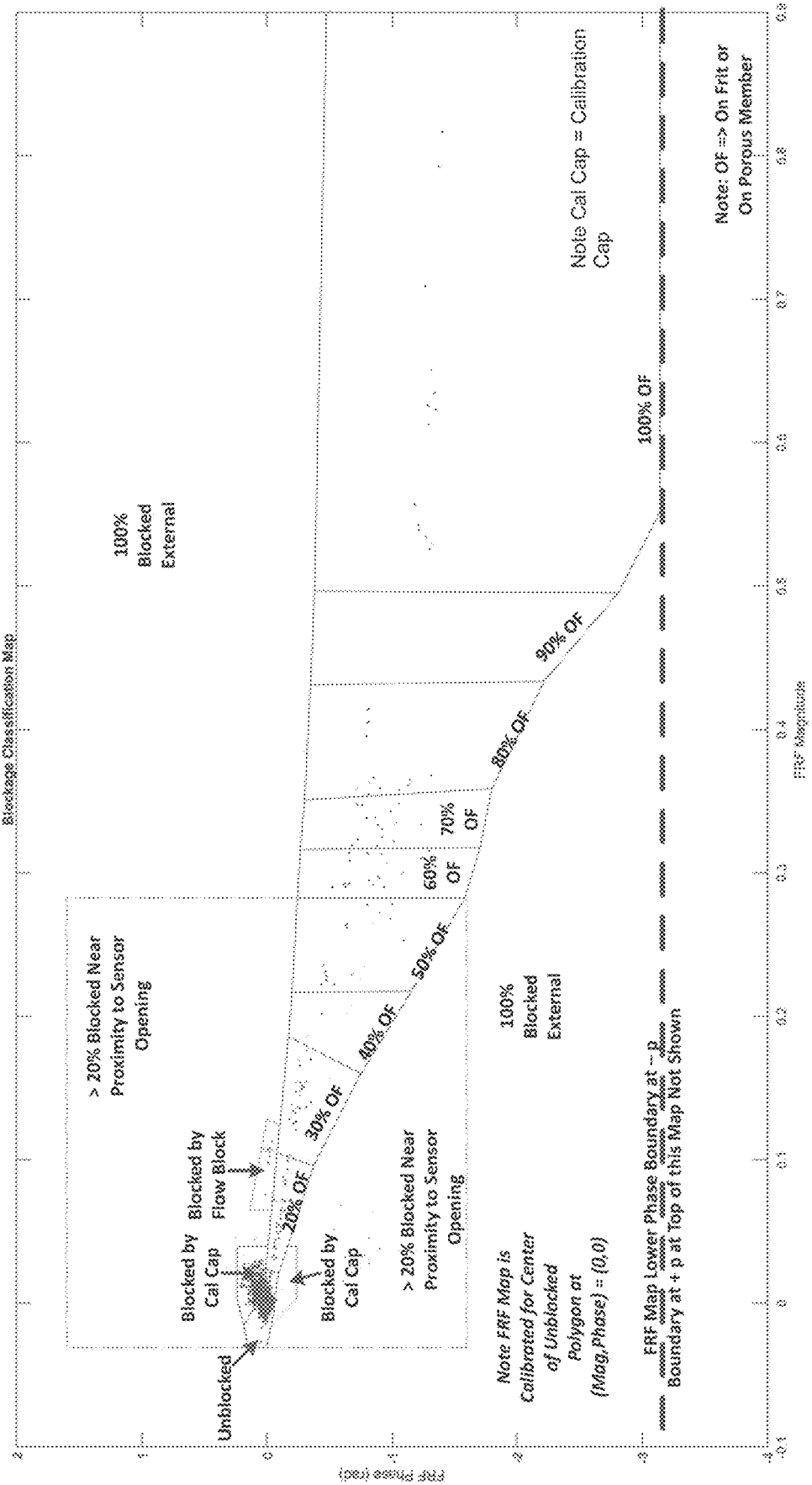
FIG. 5 illustrates an embodiment of a frequency response function (FRF) blockage classification map hereof setting forth polygons and regions bounding correlated blockage conditions such as percent blockage and/or location of blockage.

As illustrated in FIG. 5, the ability to track and cancel changes in speaker magnitude and phase afforded by the FRF facilitate creation of extensive blockage classification maps with polygons and regions identifying aspects such as percent of blockage and location of the blockage. Using such correlation maps, with each polygon or unique map region representing a discrete blockage condition, blockage may be assessed for each FRF by determining which polygon or region the FRF maps to.

Figure 6:
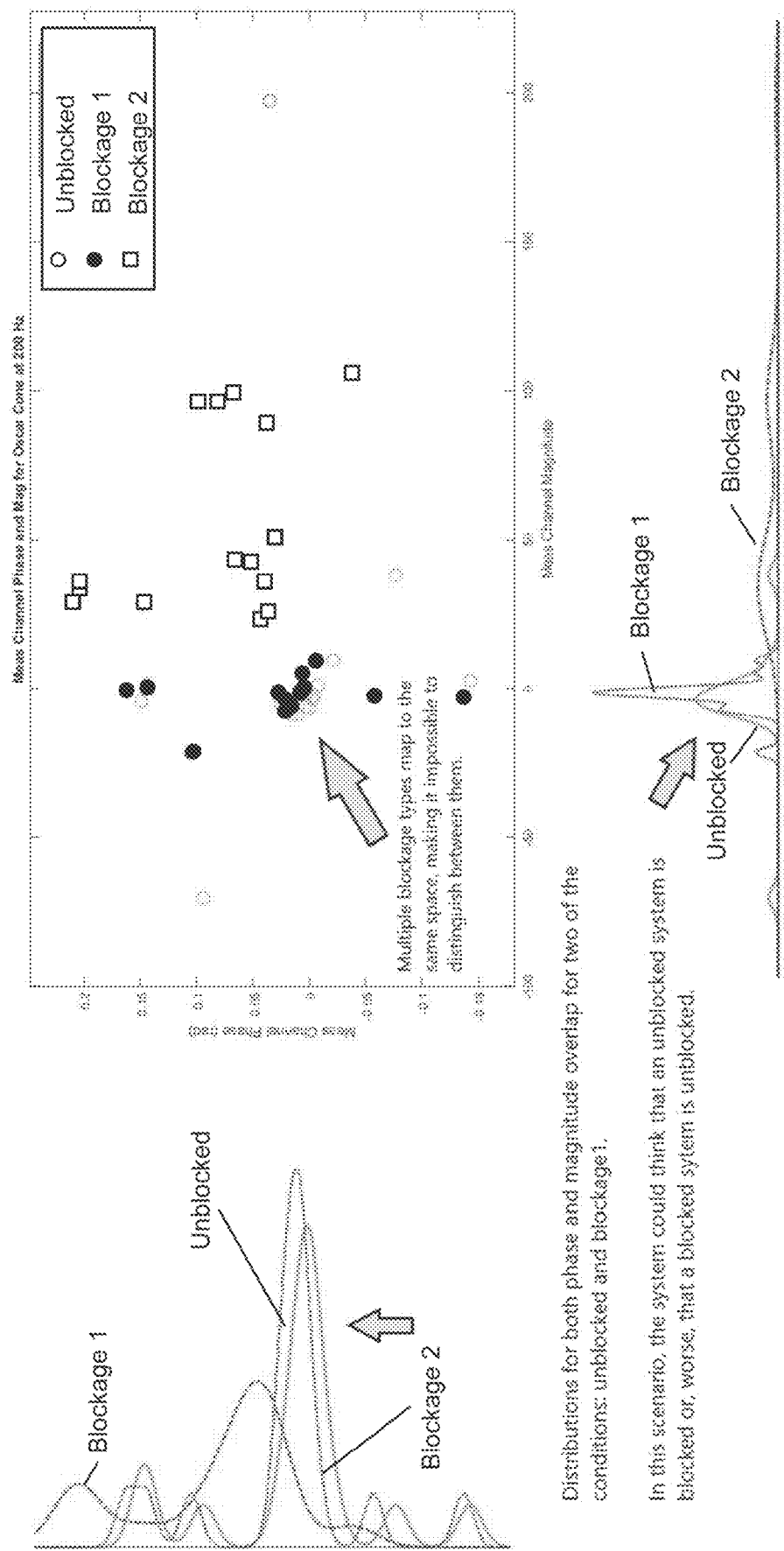
FIG. 6 illustrates a two-dimensional graph or map of magnitude and phase from a Fourier transform of a time domain response of a single (measurement channel) microphone.

For comparison, FIG. 6 illustrates a two-dimensional plot or map of data pairs of measurement channel phase and measurement channel magnitude. Once again, three different blockage states or conditions were studied. Data from a reference channel was not used in FIG. 6. Instead the magnitude M and phase θM of the DPT of the measurement channel ($X_{mic1} = M * e^{i\theta M}$) are used as the x and y coordinates respectively of the points plotted on the map in place of utilizing FRF magnitude and phase as in FIG. 3. In this case, distributions for both phase and magnitude were found to overlap for two of the blockage states (an unblocked states and a type 1 blockage state). Thus, an incorrect determination could be made that an unblocked porous member or frit is blocked or, more detrimentally, that a blocked porous member of frit is unblocked. Such confusion in blockage condition assessment can result because the magnitude and/or phase of the signal at mic 1 can be affected both by the blockage condition of the porous member and/or by acoustic loading of the speaker caused by blockages of the porous member and/or variations in speaker acoustic output due to wear and environmental factors. This is one of the significant limitations of systems that utilize the magnitude (s) and/or phase(s) from the signals of one or more microphones individually metered against prescribed thresholds or reference values as a blockage detection method. Without the ability to track and remove the component of measurement microphone signals due to speaker output changes from changes due to blockage condition response, it is difficult or impossible to establish magnitude and/or phase thresholds that definitively or uniquely separate blockage conditions of the porous member. This limitation is effectively removed when utilizing the FRF ratio of two microphone signals as prescribed in embodiments hereof. The methodology hereof removes effects of changing speaker output resulting in a response (FRF) that maps more consistently and repeatably to the same region of the classification map with regions more unique to specific blockage conditions. The improved consistency and uniqueness of the FRF magnitude and/or phase mapping overcomes those limitations inherent in individual microphone methods permitting utilization of prescribed magnitude and phase boundaries (represented for example by the rectangular polygons on the map of FIG. 3) that are less practical and reliable with individual microphone signal methods to correlate and identify blockage conditions.

In the embodiment of a device 100 hereof as illustrated in FIG. 1A, many different placements of the first microphone 160 in measurement chamber 120 and second microphone 160a within reference chamber 170 may be used in conjunction with the frequency response function and its correlation to porous member blockage as described herein. In all cases, it is advantageous to locate the first microphone 160 and second microphone 160a so that the magnitudes and/or phase coordinates of the resulting FRF ratio fall in distinct and distinguishable regions or locus on the FRF to facilitate classification or identification of blockage conditions as needed or required by a particular application as demonstrated in FIG. 3.

While not required, it is advantageous in the embodiment of device 100 to design and use the properties of wave propagation through measurement chamber 120. In that regard, one may utilize materials with acoustic impedance $Z_L$ significantly higher than the acoustic impedance of air $Z_{Air}$ into which channels are formed connecting the first microphone 160, speaker 150 and the measurement chamber 120 and second microphone 160a and speaker 150 such that the acoustic transmission through the air channels $T_{Air}=1-$ $(Z_{Air}-Z_{Air})/(Z_{Air}+Z_{Air})\sim=1$ is significantly higher than the acoustic transmission through the material $T_L=1-(Z_L-Z_{Air})/(Z_L+Z_{Air})\sim=0$ so that the magnitude of the acoustic signals reaching the first and second microphones through the air in the channels is significantly stronger than the signals reaching the first and second microphones through the material within which the air channels are formed.

FIG. 1B illustrates another embodiment of a device 100' hereof. In a number of respects, device 100' is manufactured similarly to device 100 and components thereof are numbered similarly to like components of device 100 with the addition of the designation "'" to the reference number. In the embodiment of device 100', a pressure wave source in the form of speaker 150' and a first pressure wave sensor (first sensor—measurement channel data) in the form of first microphone 160' are also positioned within a measurement volume or chamber 120'. Once again, it is not necessary to acoustically isolate speaker 150' and first microphone 160' from the remainder of chamber 120' and sensor 110' or to narrowly channel the propagation of acoustic/pressure waves therebetween. Similar to device 100, device 100' includes a second, reference microphone 160a' (second sensor—reference channel data) at a different position from first microphone 160. However, in the embodiment of FIG. 1B, each of first microphone 160' and second, reference microphone 160a' are located at different positions within measurement volume or chamber 120'.

In device 100', reference microphone is affected or excited by both the output of speaker 150' and by the blockage state of porous member or frit 150'. In the embodiment of FIG. 1B, first microphone 160' and second microphone 160a' are in the same volume of gas within measurement chamber 120' but are located or positioned at separate locations/positions therein so that responses therefrom are distinguishable in time, phase and/or amplitude. Many different placements of the first microphone and second microphone may be used in conjunction with the frequency response function and its correlation to porous member blockage as described herein. In all cases, it is advantageous to locate the first microphone 160' and second microphone 160a' so that the magnitudes and/or phase coordinates of the resulting FRF ratio fall in distinct and distinguishable regions or locus on the FRF blockage correlation map to facilitate classification or identification of blockage conditions as needed or required by a particular application as demonstrated in FIG. 3. In a number of embodiments, it is advantageous to locate the first microphone 160' so that its response changes significantly with changes in blockage of the porous member 140' while the second microphone 160a' is located to respond more significantly to the output of speaker 150'. The positioning of first microphone 160' and/or second microphone 160a' to provide discrimination of various blockage states for a particular sensor geometry is readily determinable by one skilled in the art through known engineering principles and/or routine experimentation.

In the embodiment of FIG. 1B, the properties of wave propagation through measurement chamber 120' are used. In that regard, one may utilize materials with acoustic impedance $Z_I$ significantly higher than the acoustic impedance of air $Z_{Air}$ into which channels are formed connecting the first microphone, second microphone, speaker and the measurement chamber such that the acoustic transmission through the air channels $T_{Air}=1-(Z_{Air}-Z_{Air})/(Z_{Air}+Z_{Air})\sim=1$ is significantly higher than the acoustic transmission through the material $T_L=1-(Z_L-Z_{Air})/(Z_L+Z_{Air})\sim=0$ so that the magnitude of the acoustic signals reaching the first and second microphones through the air in the channels is significantly stronger than the signals reaching the first and second microphones through material within which the air channels are formed. In a number of embodiments, it is advantageous to fashion the air channel connecting the first microphone 160' so that its response changes significantly with changes in blockage of the porous member 140' while the air channel connecting the second microphone 160a' is fashioned such that microphone 160' responds more significantly to the output of speaker 150'.

In device 100', second microphone 160a' is positioned in a port extending from measurement chamber 120'. Once again, in a number of embodiments, it is advantageous to fashion an air channel connecting the first microphone 160' so that its response changes significantly with changes in blockage of the porous member 140' and an air channel connecting the second microphone 160a' fashioned such that microphone 160' responds more significantly to the output of speaker 150'. However, such ports are not required. First microphone 160' and second microphone 160a' need only be located at separate positions within measurement chamber 120'. Once again, in all cases, it is advantageous to locate the first microphone 160' and second microphone 160a' so that the magnitudes and/or phase coordinates of the resulting FRF ratio fall in distinct and distinguishable regions or locus on the FRF blockage correlation map to facilitate classification or identification of blockage conditions as needed or required by a particular application as demonstrated in FIG. 3

FIG. 2 illustrates another embodiment of a device 100" hereof. In a number of respects, device 100" is manufactured similarly to device 100 and components thereof are numbered similarly to like components of device 100 with the addition of the designation """ to the reference number. In the embodiment of device 100", a pressure wave source in the form of speaker 150" and a first pressure wave sensor (first sensor—measurement channel data) in the form of first microphone 160" are also positioned within a measurement volume or chamber 120". Once again, it is not necessary to acoustically isolate speaker 150" and first microphone 160" from the remainder of chamber 120" and sensor 110" or to narrowly channel the propagation of acoustic/pressure waves therebetween. In contrast to device 100, device 100" replaces a second, reference microphone with element 160a" (a block schematically representing components for monitoring speaker drive voltage and/or current and computing estimates of speaker response such as back emf, impedance or correlated estimate of speaker acoustic output). The location of components and computations embodied in 160a" is not significantly important and may be distributed within the device 100" hereof. Methods for estimating speaker response parameters such as back emf, impedance and/or correlations of these estimates or measurements of speaker drive voltage and/or current to speaker acoustic output are numerous and established, and the particular approach to determining these parameters is not particular or important herein. In the context of the embodiment of FIG. 2, the parameter estimated or measured by block 160a", be it speaker voltage or current or parameters estimated from these such as back emf, impedance or correlated speaker output level, may be determined from samples taken in the same time interval or co-sampled with the signal acquired from measurement microphone 160". Using methods such as the DFT as described herein, the parameter $x_{par}$ estimated by block 160a" be it one of, for example, speaker drive current, drive voltage, back emf, impedance, speaker velocity or sound output estimation is converted into a frequency domain representation $X_{par}=I_{par}i*Q_{par}=X_{mag}*e^{i\Theta X}$. In a number of embodiments, this value then replaces the frequency response of the reference microphones ($X_{mic2}=R*e^{i\theta R}$ identified in connection with the embodiments of devices 100 and 100' of FIGS. 1A and 1B, respectively) in an FRF ratio with the response from the measurement microphone 160" ($X_{mic1}=M*e^{i\theta M}$). With this formulation, the magnitude and phase terms of the FRF mapped to the classification map may be calculated as follows:

$$FRF = X_{mic1}/X_{par}$$
$$= M*e^{i\theta M}/(X_{par}*e^{i\theta X})$$
$$= M/X_{par}e^{i(\theta M-\theta X)}$$
$$FRF \text{ Magnitude} = FRF_{mag} = M/X_{par};$$
$$FRF \text{ Phase} = FRF_{phase} = \theta M - \theta X;$$

In the embodiment of FIG. 2, first microphone 160" is in the same volume of gas within measurement chamber 120". Many different placements of the first microphone may be used in conjunction with the frequency response function and its correlation to porous member blockage described herein. In general, it is advantageous to locate the first microphone 160" so that the magnitudes and/or phase coordinates of the resulting FRF ratio with $X_{par}$ fall in distinct and distinguishable regions or locus on the FRF blockage correlation map to facilitate classification or identification of blockage conditions as needed or required by a particular application in similitude to the distinct separation of FRF points in FIG. 3. In a number of embodiments, it is advantageous to locate the first microphone 160" so that its response changes significantly with changes in blockage of the porous member 140". As in other embodiments hereof, the positioning of first microphone 160" to provide discrimination of various blockage states for a particular sensor geometry is readily determinable by one skilled in the art through known engineering principles and/or routine experimentation.

In the embodiment of FIG. 2, the properties of wave propagation through measurement chamber 120" are used. In that regard, one may utilize materials with acoustic impedance $Z_L$ significantly higher than the acoustic impedance of air $Z_{Air}$ into which channels are formed connecting the first microphone, speaker and the measurement chamber such that the acoustic transmission through the air channels $T_{Air}=1-(Z_{Air}-Z_{Air})/(Z_{Air}+Z_{Air})\sim=1$ is significantly higher than the acoustic transmission through the material $T_L=1-(Z_L-Z_{Air})/(Z_L+Z_{Air})\sim=0$ so that the magnitude of the acoustic signals reaching the first microphone through the air in the channels is significantly stronger than the signals reaching the first microphone through material within which the air channels are formed. In a number of embodiments, it is advantageous to fashion the air channel connecting the first microphone 160" so that its response changes significantly with changes in blockage of the porous member 140". In all embodiments hereof, one skilled in the art may readily determine suitable materials and channel designs for use herein using the knowledge in the art and/or routine experimentation.

Use of a second, reference microphone in the device hereof eliminates the need to rely on careful, repeatable manufacture of a speaker or speaker drive. Moreover, the second, reference microphone provides for compensation for changes in speaker output arising from changes is speaker components over time, changes in environmental conditions and/or changes in the blockage state or status of the porous member. Further, use of a second, reference microphone allows one to operate the system in a more open-loop control architecture or methodology. One may, for example, use feedback from the reference signal to drive the sound pressure level or SPL of the speaker to a specific level in a close-looped, controlled manner. Such closed-loop control systems are commonly referred to as automatic gain control (AGC). However, using data from a second, reference microphone and analytical techniques as, for example, described herein, one may allow the output levels of the speaker to float or vary. The relation of the measurement channel data and reference channel data (for example, using the ratios and FRF analysis described above) remains sufficiently consistent that feedback control is not required. Although feedback control is not necessary and adds complexity, it may be used and may, in certain embodiments, provide for improved or tighter determination specifications. In such feedback control, one may, for example, monitor the reference channel microphone output as a variable and modify the speaker drive signal as a variable to drive the reference channel signal to the same or consistent output level over time. In a number of embodiments, close-loop control may be utilized in which the reference microphone output is monitored for amplitude and/or distortion and the speaker drive level is modified to keep the response at the reference microphone within prescribed amplitude and/or distortion limits. Such control may, for example, be beneficial and necessary to prevent the speaker output from stopping or distorting as a result of changes in speaker compliance arising from environmental factors such as temperature or from changes in acoustic loading of the speaker.

Though the FRF (or other function of, for example, the output of the first (measurement) and second (reference) microphone hereof) alleviates the need to tightly control the speaker output level, in a number of embodiments, it may be advantageous to utilize feedback control in which both the reference and measurement microphones are monitored and the speaker drive signal modified to keep the responses of both microphones above their respective noise floors and below their respective saturation or clipping levels. In a number of embodiments, feedback control may be utilized in which the reference and measurement microphone signals are monitored and the speaker drive modified to maintain the response in both microphones within their respective linear or undistorted regions.

Use of parameters estimated in functional block 160a" of device 100" hereof can eliminate the need to rely on careful, repeatable manufacture of a speaker or speaker drive. Moreover, speaker response parameters estimated or measured by functional block 160a" provides for compensation for changes in speaker output arising from changes is speaker components over time, changes in environmental conditions and/or changes in the blockage state or status of the porous member. Further, use of a speaker response parameters estimated or measured by functional block 160" allows one to operate the system in a more open-loop control architecture or methodology. One may, for example, use estimates of speaker sound pressure level derived or correlated to parameters estimated or measured by functional block 160a" to drive the sound pressure level or SPL of the speaker to a specific level in a close-looped, controlled manner. However, using data or estimates of speaker response factors estimated by functional block 160a" and analytical technique such as, for example, FRF described herein, one may allow the output levels of the speaker to float or vary. The relation of the measurement microphone channel $X_{mic1}$ and parameter $X_{par}$ estimated in block 160a" (for example, using the ratios and FRF analysis described above) remains sufficiently consistent that feedback control is not required. Although feedback control is not necessary and adds complexity, it may be used and may, in certain embodiments, provide for improved or tighter determination specifications. In such feedback control, one may, for example, monitor the variable xpar or Xpar measured or estimated by functional block 160a" and modify the speaker drive signal as a variable to achieve a more consistent speaker output level over time. In a number of embodiments, close-loop control may be utilized in which the variable xpar or Xpar measured or estimated by functional block 160a" and/or the output from the measurement microphone 160" monitored and the speaker drive level modified to keep the response at the measurement microphone and/or the output of the speaker within prescribed amplitude and/or distortion limits. Such control may, for example, be beneficial and necessary to prevent the speaker output from stopping or distorting as a result of changes in speaker compliance arising from environmental factors such as temperature or from changes in acoustic loading of the speaker.

Though the FRF (or other function of the output of the first (measurement) and measured or estimated variable Xpar from functional block 160a" of device 100" hereof) alleviates the need to tightly control the speaker output level, in a number of embodiments, it may be advantageous to utilize feedback control in which the measurement microphone is monitored and the speaker drive signal modified to keep the response of the microphone above its respective noise floor and below its respective saturation or clipping levels. In a number of embodiments, feedback control may be utilized in which the measurement microphone signal is monitored and the speaker drive modified to maintain the response of microphone 1 within its linear or undistorted regions. In a number of embodiments, the response of the measurement microphone and/or the measured or estimated parameter $x_{par}$ or $X_{par}$ from block 160a" may be utilized to monitor the speaker output for distortion or clipping and the speaker drive signal modified to avoid these conditions.

In a number of embodiments, the pressure wave/acoustic interrogation devices, systems and methods hereof utilize correlation of changes in the amplitude and/or phase of the transmitter acoustic energy returned to a measurement sensor and a reference sensor, or correlation of changes in amplitude and/or phase of the transmitter response monitored by the measurement microphone and response variable $X_{par}$ monitored or estimated by functional block 160a" in the case of embodiments similar to device 100", with changes in gas permeability through a porous member or fit (and/or combined porous member and external obstructions) to infer/determine changes in restriction of gas transport (blockage) from external surroundings to/from the measurement chamber side of the porous member. A percentage of blockage may, for example, be inferred/determined or a Boolean blocked state declared based on the magnitude and/or phase change relative to the reference magnitudes and/or phases of the unblocked system. FIG. 5 illustrates utilization of such correlation with discrete blockage conditions and locations indicated by regions and polygons on a blockage FRF correlation map. In the blockage correlation map of FIG. 5, a Boolean blocked state might, for instance, be declared based on FRF points falling on or within the polygon labeled "Unblocked" being assessed as an unblocked condition while FRF points falling outside this polygon assessed as a blocked condition.

In a number of embodiments, blockage detection is significantly improved by utilizing both magnitude and phase changes of the received signal at a single or at multiple frequencies to create a multidimensional threshold scheme for discerning the blockage state of the porous member.

In a number of embodiments, the detection of magnitude and/or phase changes associated with porous member resonant frequencies and/or detection of changes in the porous member resonant frequency may be enhanced through design of the geometry of the volume(s) or chamber(s) coupling the first sensor and the second, reference sensor to the speaker and/or to the porous member. The resonant frequency of such a system may, for example, be determined by the combined acoustic impedance of the porous member and acoustic properties of the connected chamber.

Retroreflective systems as described herein offer advantages by permitting the pressure wave source/speaker and the sensors to reside within the device housing and not in the ambient environment outside of the porous member. This arrangement is especially beneficial where the porous member is used to separate hazardous or explosive environments on one side (external) from components on the other side (internal) that can be damaged or impaired by the hazardous environment or represent a potential ignition source to the external environment.

In addition to sensor output corrections associated with the electronic interrogation of a sensor as described above, devices and systems hereof may also be operable to or adapted to apply one or more corrections to sensor output determined as a result of the flow path/blockage test. In that regard, sensors may, for example, be thought of as "molecule counters". Analytical sensors are thus calibrated in a manner that a certain amount of analyte molecules react at the analytical working or sensing electrode(s) as they diffuse through the instrument and measured values are converted to, for example, a part per million (ppm) or percentage based equivalent readings based upon previous calibration. When a porous member or barrier associated with a sensor inlet is open and unobstructed, rates of diffusion are very repeatable under the same conditions. As a porous member becomes blocked or flow paths are otherwise obstructed, the rate at which the molecules can diffuse from outside the instrument housing to the sensor can slow, thus lowering the rate at which molecules will encounter the active portion of the sensor, and in certain embodiments thereby lowering the output. By measuring partial blockages as a result of one or more tests hereof, one can adjust the sensitivity of the sensor to maintain accurate readings regardless of such partial blockages.

Percent blockage may, for example, be readily experimentally correlated with a correction factor. An associated lookup table or an associated algorithm/formula may, for example, be stored in memory of the device and systems hereof, and a correction factor for sensor sensitivity may be determined therefrom.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method of detecting at least a blockage status in a porous member separating a measurement chamber of a device including a gas sensor positioned within the measurement chamber which is responsive to an analyte in an ambient environment to be sampled, comprising:
emitting pressure waves from a pressure wave source which travel within the measurement chamber, measuring a first response via a first sensor responsive to pressure waves positioned at a first position within the measurement chamber, measuring a second response via a second sensor at a second position, different from the first position, and in fluid connection with the pressure wave source, determining the blockage status of the porous member based upon a functional relation of the first response and the second response.

2. The method of claim 1 wherein the second sensor is used as a reference sensor.

3. The method of claim 2 wherein the pressure wave source includes a speaker and emitting pressure waves which travel within the measurement chamber comprises activating the speaker to emit sound waves within the measurement chamber, the first sensor comprises a first microphone, and the second sensor comprises a second microphone.

4. The method of claim 3 wherein the second position of the second sensor is within a reference chamber that is separated from the measurement chamber but in fluid connection with the speaker.

5. The method of claim 4 wherein the reference chamber is separated from the measurement chamber by the speaker.

6. The method of claim 3 wherein the second position of the second sensor is within the measurement chamber.

7. The method of claim 1 wherein the first response and the second response are measured in the time domain over a period of time and the measured time domain responses are transformed into a frequency domain.

8. The method of claim 7 wherein at least one of amplitude and phase is determined for each of the first sensor and the second sensor at a frequency.

9. The method of claim 8 further comprising determining a ratio of the at least one of the amplitudes and the phases measured by the first sensor and the second sensor.

10. The method of claim 9 further comprising determining a ratio of each of the amplitudes and the phases measured by the first sensor and the second sensor.

11. The method of claim 10 further comprising comparing a two-dimensional map of the determined ratios of the amplitude and the phase to a previously determined reference map to determine the blockage status of the porous member.

12. The method of claim 11 wherein determining the blockage status of the porous member comprises at least one of determining a degree of blockage or a type of blockage in the porous member.

13. The method of claim 1 further comprising using a feedback signal from the second sensor to drive a pressure level of the source of pressure waves to a determined level in a closed-looped, control methodology.

14. A gas sensor device to detect an analyte gas in an ambient environment, comprising:
a housing comprising a measurement chamber and a port;
a porous member in operative connection with the port to separate the measurement chamber from the ambient environment;
a sensor responsive to the analyte gas positioned within the measurement chamber;
a source of pressure waves positioned within the measurement chamber;
a first sensor responsive to pressure waves at a first position within the measurement chamber;
a second sensor responsive to pressure waves positioned at a second position, different from the first position, and in fluid connection with the source of pressure waves, and
circuitry in operative connection with the first sensor and the second sensor to determine a blockage status of the porous member based upon a functional relation of a response of the first sensor and a response of the second sensor.

15. The device of claim 14 wherein the second sensor is used as a reference sensor.

16. The device of claim 15 wherein the source of pressure waves comprises a speaker which emits sound waves when activated, the first sensor comprises a first microphone, and the second sensor comprises a second microphone.

17. The device of claim 16 wherein the second position of the second sensor is within a reference chamber that is separated from the measurement chamber but in fluid connection with the speaker.

18. The device of claim 17 wherein the reference chamber is separated from the measurement chamber by the speaker.

19. The device of claim 18 wherein a ratio of response of the first sensor and the second sensor is determined via the circuitry.

20. The device of claim 19 wherein the circuitry compares the determined ratios of the measured amplitudes and the measured phases to a previously determined reference map to determine the blockage status of the porous member.

21. The device of claim 20 wherein determining the blockage status of the porous member comprises at least one of determining a degree of blockage or a type of blockage in the porous member.

22. The device of claim 16 wherein the second position of the second sensor is within the measurement chamber.

23. The device of claim 14 wherein the first response and the second response are measured in the time domain over a period of time via the circuitry and the measured time domain responses are transformed into a frequency domain.

24. The device of claim 23 wherein at least one of amplitude and phase is determined for each of the first sensor and the second sensor at a frequency.

25. The device of claim 24 wherein the circuitry determines a ratio of the at least one of the measured amplitudes and the measured phases of the first sensor and the second sensor.

26. The device of claim 24 wherein the circuitry determines a ratio of each of the measured amplitudes and the measured phases of the first sensor and the second sensor.

27. The device of claim 14 wherein the circuitry comprises a processor system in operative connection with a memory system.

28. The device of claim 14 wherein the circuitry is further configured to use a feedback signal from the second sensor to drive a pressure level of the source of pressure waves to a determined level in a closed-looped, control methodology.

* * * * *